United States Patent
Engel et al.

(10) Patent No.: US 10,682,307 B2
(45) Date of Patent: Jun. 16, 2020

(54) GASTRIC RETENTION ACTIVE DELIVERY SYSTEMS

(71) Applicant: Evonik Operations GmbH, Essen (DE)

(72) Inventors: Andrea Engel, Frankfurt (DE); Thomas Gottstein, Babenhausen (DE); Melanie Liefke, Ober-Ramstadt (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 15/774,395

(22) PCT Filed: Oct. 27, 2016

(86) PCT No.: PCT/EP2016/075872
§ 371 (c)(1),
(2) Date: May 8, 2018

(87) PCT Pub. No.: WO2017/080833
PCT Pub. Date: May 18, 2017

(65) Prior Publication Data
US 2019/0282493 A1    Sep. 19, 2019

(30) Foreign Application Priority Data

Nov. 10, 2015 (EP) ................................... 15193887

(51) Int. Cl.
| | |
|---|---|
| *A61K 9/46* | (2006.01) |
| *A61K 9/00* | (2006.01) |
| *A61K 9/48* | (2006.01) |
| *A61K 31/05* | (2006.01) |
| *A61K 36/185* | (2006.01) |

(52) U.S. Cl.
CPC .......... *A61K 9/0007* (2013.01); *A61K 9/0065* (2013.01); *A61K 9/485* (2013.01); *A61K 9/4816* (2013.01); *A61K 9/4825* (2013.01); *A61K 9/4858* (2013.01); *A61K 9/4866* (2013.01); *A61K 9/4891* (2013.01); *A61K 31/05* (2013.01); *A61K 36/185* (2013.01)

(58) Field of Classification Search
None
See application file for complete search history.

(56) References Cited

U.S. PATENT DOCUMENTS

| | | | |
|---|---|---|---|
| 6,699,506 B1 * | 3/2004 | Paillard ............... | A61K 9/1652 424/400 |
| 9,492,394 B2 * | 11/2016 | Bodinge ............. | A61K 9/2846 |
| 2008/0107732 A1 | 5/2008 | Dharmadhikari et al. | |
| 2010/0055133 A1 * | 3/2010 | Duffield .............. | A61K 9/2054 424/239.1 |
| 2011/0200671 A1 | 8/2011 | Dharmadhikari et al. | |
| 2014/0105973 A1 | 4/2014 | Dharmadhikari et al. | |

FOREIGN PATENT DOCUMENTS

EP    1 732 522 B1    12/2006

OTHER PUBLICATIONS

International Search Report and Written Opinion dated Jan. 16, 2017, in PCT/EP2016/075872, filed Oct. 27, 2016.

* cited by examiner

*Primary Examiner* — Jeffrey T. Palenik
(74) *Attorney, Agent, or Firm* — Oblon, McClelland, Maier & Neustadt, L.L.P.

(57) ABSTRACT

The present invention relates to a gastric retention active delivery system in the form of a coated capsule, which, in contrast to prior art delivery systems exhibiting relatively poor floating-properties, and thus requiring size expansion capability in order to securely delay passage through the pylorus, reliably stay afloat for several hours. This is achieved by combining pore forming components and flexible polymer components in the coating in suitable proportions. The present invention, further, relates to the use of gastric retention active delivery systems of the invention for the delivery of one or more water soluble active components A to a mammal.

16 Claims, No Drawings

GASTRIC RETENTION ACTIVE DELIVERY SYSTEMS

Administration of active ingredients that are stable in acidic environments and absorbed in the stomach or proximal parts of the small intestine may beneficially be performed using formulations for gastric release. Accordingly, numerous dosage forms for gastric release have been developed in the past. Prompted by the short and highly variable time intervals available for absorption in the stomach due to gastric emptying floating delivery systems were developed that are capable of maintaining presence in the stomach for extended periods of time, thus, providing long and reliable intervals for gastric absorption. A number of floating delivery systems known in the art are based on matrix formulations. However, as these systems usually require manufacture under wet granulation conditions, they cannot be applied for moisture sensitive ingredients. EP1732522B1 discloses gastric retention devices in the form of coated capsules that could be applied for moisture sensitive ingredients. The delivery systems of EP1732522B1 exhibit relatively poor floating-capabilities, with floating times below 1 hour, which, however, are compensated by size expansion behavior of the devices when exposed to gastric fluid, thus, reliably delaying passage through the pylorus for extended periods of time after floating has ceased. The structural layout of the delivery systems of EP1732522B1, however, is fairly complex and thus unattractive for a number of applications from a commercial point of view.

In view of the above there is a need in the art for gastric retention active delivery systems applicable for moisture sensitive ingredients and displaying a simpler structural layout.

This problem is solved by the gastric retention active delivery systems according to the present invention, in the form of a coated capsule, comprising a sealed capsule encasing an effervescent formulation of one or more water soluble active components A, and a coating;
wherein the coating comprises:
  a total amount $px$ of one or more pore forming components P, with $px$ selected in the interval $p1 < px < p2$, wherein $p1 = 1$ mg/cm$^2$ and $p2 = 11$ mg/cm$^2$;

a total amount $fx$ of one or more flexible polymer components F, with $fx$ selected in the interval $f1 < fx < f2$, wherein $f1 = 4$ mg/cm$^2$ and $f2 = 10$ mg/cm$^2$, and wherein, further, $0.453 \cdot px + 3.49$ mg/cm$^2 < fx < 0.625 \cdot px + 4.75$ mg/cm$^2$;

a total amount $ex$ of one or more amphiphilic emulsifier components E, with $ex$ selected in the interval $e1 < ex < e2$, wherein $e1 = 0$ and $e2 = 0.1 \cdot fx$;

a total amount $tx$ of one or more anti-tacking components T, with $tx$ selected in the interval $t1 < tx < t2$, wherein $t1 = 0.5 \cdot fx$ and $t2 = 2 \cdot fx$;

a total amount $nx$ of one or more non-water soluble excipients N, with $nx$ selected in the interval $n1 < nx < n2$, wherein $n1 = 0$ and $n2 = 0.1 \cdot fx$;

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;

wherein pore forming components P are defined as water soluble substances, including active components A, but excluding amphiphilic emulsifier components E;

wherein, further, the effervescent formulation inside of the sealed capsule exhibits a gas generating capacity in the range of 60 Vol % to 140 Vol % of the total volume of the sealed capsule at 25° C. and 1013 mbar.

As indicated above, in contrast to prior art delivery systems (cf. EP1732522B1) exhibiting relatively poor floating-properties, and thus requiring size expansion capability in order to securely delay passage through the pylorus, delivery systems of the present invention reliably stay afloat for several hours. This is achieved (cf. experimental section) by combining pore forming components P and flexible polymer components F in the coating in suitable proportions. If the amount of pore forming components is too high and the amount of flexible polymer components is too low, release from the capsule will be vigorous and uneven and buildup of excessive internal gas pressure may compromise the structural integrity of the capsule. If the amount of pore forming components is too low and the amount of flexible polymer components is too high, release from the capsule will be protracted and a lack of sufficient internal gas pressure may result in the capsule not being able to reliably stay afloat for sufficient periods of time. Therefore, pore forming components P and flexible polymer components F are combined in the coating in the following proportions:

The total amount $px$ of all pore forming components P in the coating combined is chosen such that $px$ is selected in the interval $p1 < px < p2$, wherein $p1 = 1$ mg/cm$^2$ and $p2 = 11$ mg/cm$^2$; and $fx$ the total amount of dry substance of all flexible polymer components F in the coating combined is chosen such that $fx$ is selected in the interval $f1 < fx < f2$, wherein $f1 = 4$ mg/cm$^2$ and $f2 = 10$ mg/cm$^2$, and wherein, further, $fx$ is selected within the following boundaries $0.453 \cdot px + 3.49$ mg/cm$^2 < fx < 0.625 \cdot px + 4.75$ mg/cm$^2$.

In preferred embodiments of the present invention, $px$ is selected in the interval $p1 < px < p2$, wherein $p1 = 2$ mg/cm$^2$ and $p2 = 8$ mg/cm$^2$.

In further preferred embodiments of the present invention, $fx$ is selected in the interval $f1 < fx < f2$, wherein $f1 = 4.5$ mg/cm$^2$ and $f2 = 8.5$ mg/cm$^2$, and wherein, further, $0.453 \cdot px + 3.49$ mg/cm$^2 < fx < 0.625 \cdot px + 4.75$ mg/cm$^2$.

In other preferred embodiments of the present invention $px$ is selected in the interval $p1 < px < p2$, wherein $p1 = 2$ mg/cm$^2$ and $p2 = 8$ mg/cm$^2$ and $fx$ is selected in the interval $f1 < fx < f2$, wherein $f1 = 4.5$ mg/cm$^2$ and $f2 = 8.5$ mg/cm$^2$, and wherein, further, $0.453 \cdot px + 3.49$ mg/cm$^2 < fx < 0.625 \cdot px + 4.75$ mg/cm$^2$.

If the amount of pore forming components is too high and the amount of flexible polymer components is too low, release from the capsule will be vigorous and uneven and buildup of excessive internal gas pressure may compromise the structural integrity of the capsule. If the amount of pore forming components is too low and the amount of flexible polymer components is too high, release from the capsule will be protracted.

In the context of the present invention the term pore forming components P relates to water soluble substances that allow pores to be introduced into the coating or permeability of the coating to be increased, thus facilitating diffusion controlled release of active ingredients from the sealed capsule. Non-amphiphilic substances that can be dissolved in water at 25° C. and pH 1.2 at a concentration of at least 33 g per liter of water are considered as pore forming components P in the present context. Accordingly, the term pore forming components P comprises non-amphiphilic excipients that can be dissolved in water at 25° C. and pH 1.2 at a concentration of at least 33 g per liter of water. Amphiphilic emulsifiers E, however, are not considered as pore forming components in the present context, since such amphiphilic emulsifiers would not facilitate pore formation but dissolve in and thus become attached to the flexible polymer components F of the coating instead due to their amphiphilic character. Non-amphiphilic water soluble active components A, on the other hand, that are present in the coating, are considered as pore forming components. According to the current invention one or more pore forming components P may be present in the coating.

In the context of the present invention suitable pore forming components P may be selected from the following: Non-amphiphilic water soluble active components A; water soluble organic or inorganic salts of magnesium, sodium, calcium, potassium, lithium, ammonium; water soluble cellulose ethers; water soluble organic acids or alpha-hydroxy acids including citric acid, oxalic acid, malic acid, mandelic acid, glycolic acid, tartaric acid, fumaric acid; water-soluble sugars including polydextrose, pullulan, dextran, sucrose, glucose, fructose, mannitol, lactose, mannose, galactose, rhamnose, sorbitol, maltodextrin, trehalose, xylitol. In preferred embodiments of the present invention pore forming components P are selected from the following: Maltodextrin; citric acid; non-amphiphilic water soluble active components A including extracts of fruits and/or flowers (including extracts of elderberry, bilberry and blackcurrant), polyphenols, anthocyanins. In further preferred embodiments of the present invention pore forming components P are selected from the following: Derivatives of cyanidin, delphinidin, isopeonidin, peonidin, malvidin, pelargonidin, and petunidin; maltodextrin; citric acid. In further preferred embodiments of the present invention pore forming components P are selected from the following: Maltodextrin; citric acid; compounds derived from cyanidin, delphinidin, isopeonidin, peonidin, malvidin, pelargonidin and petunidin by substituting one or more hydroxyl groups with a mono- or oligosaccharide comprising the following sugars: Glucose, rhamnose, galactose, rutinose, arabinose. In further preferred embodiments of the present invention pore forming components P are selected from the following compounds or derivatives thereof: Cyanidin, delphinidin, isopeonidin, peonidin, malvidin, pelargonidin, petunidin; wherein the derivatives are obtained by substituting one or more hydroxyl groups with a mono- or oligosaccharide comprising the following sugars: Glucose, rhamnose, galactose, rutinose, arabinose.

In the context of the present invention the term flexible polymer components F relates to neutral or virtually neutral (meth)acrylate copolymers composed of 20 wt % to 40 wt % of ethyl acrylate, 60 wt % to 80 wt % of methyl methacrylate and 0 to less than 5 wt %, of methacrylic acid or acrylic acid. According to the current invention one or more flexible polymer components F may be present in the coating.

In the context of the present invention suitable flexible polymer components F include but are not limited to the following: Eudragit® NE 30 D, Eudragit® NE 40 D, Eudragit® NM 30 D, Eudraguard® control (all of which are available commercially).

In preferred embodiments of the present invention flexible polymer components F are neutral or virtually neutral (meth)acrylate copolymers composed of 20 wt % to 40 wt % of ethyl acrylate, 60 wt % to 80 wt % of methyl methacrylate and 0 to 2 wt % of methacrylic acid or acrylic acid.

In further preferred embodiments of the present invention flexible polymer components F are neutral or virtually neutral (meth)acrylate copolymers composed of 20 wt % to 40 wt % of ethyl acrylate, 60 wt % to 80 wt % of methyl methacrylate and 0.05 wt % to 1 wt % of methacrylic acid or acrylic acid.

In preferred embodiments, the present invention relates to gastric retention active delivery systems in the form of a coated capsule, comprising a sealed capsule encasing an effervescent formulation of one or more water soluble active components A, and a coating comprising an initial dose ID of at least one of the water soluble active components A present within the sealed capsule;

wherein the coating comprises:

a total amount px of one or more pore forming components P, with px selected in the interval $p1<px<p2$, wherein $p1=1$ mg/cm$^2$ and $p2=11$ mg/cm$^2$;

a total amount fx of one or more flexible polymer components F, with fx selected in the interval $f1<fx<f2$, wherein $f1=4$ mg/cm$^2$ and $f2=10$ mg/cm$^2$, and wherein, further, $0.453*px+3.49$ mg/cm$^2 <fx< 0.625*px+4.75$ mg/cm$^2$;

a total amount ex of one or more amphiphilic emulsifier components E, with ex selected in the interval $e1<ex<e2$, wherein $e1=0$ and $e2=0.1*fx$;

a total amount tx of one or more anti-tacking components T, with tx selected in the interval $t1<tx<t2$, wherein $t1=0.5*fx$ and $t2=2*fx$;

a total amount nx of one or more non-water soluble excipients N, with nx selected in the interval $n1<nx<n2$, wherein $n1=0$ and $n2=0.1*fx$;

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;

wherein pore forming components P are defined as water soluble substances, including active components A, but excluding amphiphilic emulsifier components E; wherein the initial dose ID, of at least one water soluble active component A present in the coating constitutes 5 wt % to 50 wt % of the total amount of this component present in the gastric retention active delivery system;

wherein, further, the effervescent formulation inside of the sealed capsule exhibits a gas generating capacity in the range of 60 Vol % to 140 Vol % of the total volume of the sealed capsule at 25° C. and 1013 mbar.

An advantage of such preferred delivery systems of the present invention resides in the fact that those active components A, of which an initial dose ID is present in the coating in addition to the dose present within the sealed capsule, exhibit a rapid onset of release. Accordingly, most of the time of presence in the stomach, i.e. the time interval available for gastric release, can be utilized for the delivery of such active components.

Corresponding delivery systems of the present invention are, thus, not only capable of maintaining long and reliable presence in the stomach but, additionally, enable efficient utilization of these time intervals for the release of active components. As a result, delivery profiles that are very evenly distributed can be obtained with such delivery systems of the present invention.

More specifically, delivery systems of the present invention wherein the coating comprises an initial dose ID of at least one of the water soluble active components A present within the sealed capsule wherein the initial dose ID, of at least one water soluble active component A present in the coating constitutes 5 wt % to 50 wt % of the total amount of this component present in the gastric retention active delivery system, release such water soluble active components A, of which such an initial dose ID is present in the coating, with a release profile defined as follows: Release of 5% to 55% of the total amount present in the gastric retention system at t=105 min after administration; and release of 47%-96% of the total amount present in the gastric retention system at t=180 min after administration; and release of 70%-100% of the total amount present in the gastric retention system at t=240 min after administration.

In preferred embodiments of the present invention the coating comprises an initial dose ID of at least one of the water soluble active components A present within the sealed capsule wherein the initial dose ID, of at least one water soluble active component A present in the coating constitutes 20 wt % to 40 wt % of the total amount of this component present in the gastric retention active delivery system Water soluble active components A according to the present invention are defined as non-amphiphilic substances that can be dissolved in water at 25° C. and pH 1.2 at a concentration of at least 33 g per liter of water. According to the current invention one or more water soluble active components A may be present in the coating and/or the sealed capsule.

In preferred embodiments of the present invention at least one of the water soluble active components A is a non-amphiphilic substance of synthetic origin that can be dissolved in water at 25° C. and pH 1.2 at a concentration of at least 33 g per liter of water. In other preferred embodiments of the present invention at least one of the water soluble active components A is a non-amphiphilic substance obtainable from microbial fermentation that can be dissolved in water at 25° C. and pH 1.2 at a concentration of at least 33 g per liter of water. In other preferred embodiments of the present invention at least one of the water soluble active components A is a non-amphiphilic vitamin that can be dissolved in water at 25° C. and pH 1.2 at a concentration of at least 33 g per liter of water. In other preferred embodiments of the present invention at least one of the water soluble active components A is a non-amphiphilic micronutrient that can be dissolved in water at 25° C. and pH 1.2 at a concentration of at least 33 g per liter of water. In other preferred embodiments of the present invention at least one of the water soluble active components A is a non-amphiphilic inorganic salt that can be dissolved in water at 25° C. and pH 1.2 at a concentration of at least 33 g per liter of water. In other preferred embodiments of the present invention at least one of the water soluble active components A is a non-amphiphilic amino acid or keto acid that can be dissolved in water at 25° C. and pH 1.2 at a concentration of at least 33 g per liter of water. In other preferred embodiments of the present invention at least one of the water soluble active components A is a non-amphiphilic trace element that can be dissolved in water at 25° C. and pH 1.2 at a concentration of at least 33 g per liter of water. In other preferred embodiments of the present invention at least one of the water soluble active components A is a non-amphiphilic dye that can be dissolved in water at 25° C. and pH 1.2 at a concentration of at least 33 g per liter of water. In other preferred embodiments of the present invention at least one of the water soluble active components A is a non-amphiphilic antacid that can be dissolved in water at 25° C. and pH 1.2 at a concentration of at least 33 g per liter of water. In other preferred embodiments of the present invention at least one of the water soluble active components A is a non-amphiphilic substance obtainable from plant extracts that can be dissolved in water at 25° C. and pH 1.2 at a concentration of at least 33 g per liter of water. In other preferred embodiments of the present invention at least one of the water soluble active components A is a non-amphiphilic substance obtainable from extracts of fruits and/or flowers that can be dissolved in water at 25° C. and pH 1.2 at a concentration of at least 33 g per liter of water. In other preferred embodiments of the present invention at least one of the water soluble active components A is a non-amphiphilic substance obtainable from extracts of elderberry, bilberry and/or blackcurrant that can be dissolved in water at 25° C. and pH 1.2 at a concentration of at least 33 g per liter of water. In other preferred embodiments of the present invention at least one of the water soluble active components A is a non-amphiphilic compound that can be dissolved in water at 25° C. and pH 1.2 at a concentration of at least 33 g per liter of water and which is selected from the following compounds or non-amphiphilic derivatives thereof: Cyanidin, delphinidin, isopeonidin, peonidin, malvidin, pelargonidin, petunidin. In other preferred embodiments of the present invention at least one of the water soluble active components A is a non-amphiphilic compound that can be dissolved in water at 25° C. and pH 1.2 at a concentration of at least 33 g per liter of water, and that can be derived from cyanidin, delphinidin, isopeonidin, peonidin, malvidin, pelargonidin or petunidin by substituting one or more hydroxyl groups with a mono- or oligosaccharide comprising the following sugars: Glucose, rhamnose, galactose, rutinose, arabinose. In further preferred embodiments of the present invention at least one of the water soluble active components A is a non-amphiphilic polyphenol that can be dissolved in water at 25° C. and pH 1.2 at a concentration of at least 33 g per liter of water. In other preferred embodiments of the present invention at least one of the water soluble active components A is a non-amphiphilic anthocyanin that can be dissolved in water at 25° C. and pH 1.2 at a concentration of at least 33 g per liter of water. In yet other preferred embodiments of the present invention all of the water soluble active components A are non-amphiphilic compounds that can be dissolved in water at 25° C. and pH 1.2 at a concentration of at least 33 g per liter of water, and that can be derived from cyanidin, delphinidin, isopeonidin, peonidin, malvidin, pelargonidin or petunidin by substituting one or more hydroxyl groups with a mono- or oligosaccharide comprising the following sugars: Glucose, rhamnose, galactose, rutinose, arabinose. In yet other preferred embodiments of the present invention all of the water soluble active components A are non-amphiphilic compounds that can be dissolved in water at 25° C. and pH 1.2 at a concentration of at least 33 g per liter of water, and that are selected from the following compounds or derivatives thereof: Cyanidin, delphinidin, isopeonidin, peonidin, malvidin, pelargonidin, petunidin; wherein the derivatives are obtained by substituting one or more hydroxyl groups with a mono- or oligosaccharide comprising the following sugars: Glucose, rhamnose, galactose, rutinose, arabinose.

According to the present invention the coating, further, comprises a total amount ex of one or more amphiphilic emulsifier components E, with ex selected in the interval e1<ex<e2, wherein e1=0 and e2=0.1*fx; i.e. the total amount ex of one or more amphiphilic emulsifier components E is selected in the range of 0 to 10 wt % of fx (with fx denoting the total amount of dry substance of all flexible polymer components F in the coating combined). The function of amphiphilic emulsifier components E in the coating resides in stabilizing the coating dispersion against coagulation of the film forming polymer as well as phase separation, and thus allowing uniform and even coatings to be obtained. Amphiphilic emulsifier components E of the present invention have to be capable of performing this function at a concentration not exceeding 10 wt % of fx, with fx denoting the total amount of dry substance of all flexible polymer components F in the coating combined.

Accordingly, in the context of the present invention, amphiphilic emulsifier components E are defined as non-ionic emulsifiers with an HLB-value greater than 14 (HLB=hydrophilic-lipophilic balance according Griffin as defined in Hagers Handbuch der Pharmazeutischen Praxis (ISBN 978-3-642-61249-7), Band 2, Methoden, Kapitel 4.1). In preferred embodiments amphiphilic emulsifier components E are defined as non-ionic emulsifiers with an HLB-value in the range of 14 to 29. In other preferred embodiments amphiphilic emulsifier components E are defined as non-ionic emulsifiers with an HLB-value in the range of 14 to 24. According to the current invention one or more amphiphilic emulsifier components E may be present in the coating.

In the context of the present invention suitable amphiphilic emulsifier components E may be selected from the following: Polysorbates (Tween® series), polyoxyethylated glycol monoethers (like the Brij® series), polyoxyethylated alkyl phenols (like the Triton® series or the Igepal series). In preferred embodiments of the present invention amphiphilic emulsifier components E are selected from the following: Polysorbate 80, Poloxamer 188.

According to the present invention the coating, further, comprises a total amount tx of one or more anti-tacking components T, with tx selected in the interval t1<tx<t2, wherein t1=0.5*fx and t2=2*fx; i.e. the total amount tx of one or more anti-tacking components T is selected in the range of 50 wt % to 200 wt % of fx (with fx denoting the total amount of dry substance of all flexible polymer components F in the coating combined). In the present context anti-tacking components T are defined as excipients that are insoluble in water (solubility in water at 25° C. and pH 1.2 below 0.1 g per liter of water) and chemically inert under the conditions experienced by the delivery system of the invention and its components during processing and which may be added to the coating formulation in order to expedite processing by avoiding problems related to agglomeration of coated capsules during the coating process. According to the current invention one or more anti-tacking components T may be present in the coating.

In the context of the present invention suitable anti-tacking agents T include talc, glyceryl monostearate, kaoline, fumed silica, precipitated silica, magnesium stearate, calcium stearate, zinc stearate. In preferred embodiments of the present invention anti-tacking agents T are selected from the following: Talc, magnesium stearate, kaolin.

In a preferred embodiment of the present invention tx is selected in the interval t1<tx<t2, wherein t1=0.7*fx and t2=1.5*fx; i.e. the total amount tx of one or more anti-tacking components T is selected in the range of 70 wt % to 150 wt % of fx (with fx denoting the total amount of dry substance of all flexible polymer components F in the coating combined).

According to the present invention the coating, further, comprises a total amount nx of one or more non-water soluble excipients N, with nx selected in the interval n1<nx<n2, wherein n1=0 and n2=0.1*fx; i.e. the total amount nx of one or more non-water soluble excipients N is selected in the range of 0 to 10 wt % of fx (with fx denoting the total amount of dry substance of all flexible polymer components F in the coating combined). In the present context non-water soluble excipients N are defined as excipients that are insoluble in water (solubility in water at 25° C. and pH 1.2 below 0.1 g per liter of water) and that a person of skill in the art would not normally add to the coating formulation in order to avoid problems related to agglomeration of coated capsules during the coating process, i.e. non-water soluble excipients N do not include anti tacking components T. According to the current invention one or more non-water soluble excipients N may be present in the coating.

In the context of the present invention suitable non-water soluble excipients N include pigments and non-water-soluble flavours. In preferred embodiments of the present invention non-water soluble excipients N are selected from the following: Iron oxides, aluminium lakes, titanium dioxide.

The gastric retention active delivery system of the present invention exhibits the form of a coated capsule, comprising a sealed capsule encasing an effervescent formulation of one or more water soluble active components A, and a coating enclosing the sealed capsule.

According to the present invention the sealed capsule may be any capsule wherein the two members of the capsule are sealed together hermetically in order to prevent accidental separation and access of air and moisture. Typically the sealing may be achieved by providing a subcoat or encircling band. Capsule and sealing may preferably be made from the same material, however, embodiments where this is not the case are also comprised by the present invention.

Capsule and/or sealing may be made from the following materials: Hydroxypropyl methylcellulose (HPMC), gelatin, pullulan, or starch. In a preferred embodiment of the present invention capsule and/or sealing are composed of hydroxypropyl methylcellulose (HPMC) or gelatin. In another preferred embodiment of the present invention the sealing is composed of an acetylated pre-gelled starch containing at least 50 wt % of amylose and having a percentage of acetylic groups of 0.5 wt % to 2.5 wt %. In another preferred embodiment of the present invention the sealing of the sealed capsule exhibits a surface density of 5 mg/cm$^2$-15 mg/cm$^2$.

Sealed capsules may be coated with a standard fluid bed coater under controlled flow conditions as described in Pharmazeutische Technologie, Bauer, Frömming, Führer, 9.Auflage (ISBN 978-3-8047-2552-2).

The gas generating capacity of the effervescent formulation inside of the sealed capsule specifies the theoretical maximum of the volume of gas, measured at 25° C. and 1013 mbar, that can be released from the gas generating agents present in the effervescent formulation when used in a gastric retention active delivery system. The gas generating capacity of the effervescent formulation inside of the sealed capsule must be chosen in suitable proportion to the interior volume of the sealed capsule (cf. experimental section). If the gas generating capacity is too low, internal gas pressure may be insufficient to expel fluids entering the interior of the capsule, and thus the capsule may not be able to reliably stay afloat for sufficient periods of time. If, on the other hand, the gas generating capacity is too high, ruptures of sealing and/or coating resulting from excessive internal gas pressure may compromise the structural integrity of the capsule, resulting in aberrant floating and release behavior. Therefore, the effervescent formulation inside of the sealed capsule of the gastric retention active delivery system of the present invention should exhibit a gas generating capacity in the range of 60 Vol % to 140 Vol % of the total volume of the sealed capsule at 25° C. and 1013 mbar.

According to the present invention the effervescent formulation inside of the sealed capsule comprises gas generating agents. In the presence of an acid and when contacted with water these gas generating agents release carbon dioxide. Suitable gas generating agents according to the present invention may be selected from the following: One or more carbonate salts, one or more bicarbonate salts, mixtures of one or more carbonate salts, mixtures of one or more bicarbonate salts, mixtures of one or more carbonate salts with one or more bicarbonate salts. In preferred embodiments of the present invention the gas generating agents are selected from the following: sodium carbonate, sodium bicarbonate, potassium carbonate, potassium bicarbonate, magnesium carbonate, calcium carbonate. The acid component according to the present invention may be gastric acid entering the capsule interior and/or may consist of one or more organic or inorganic acids included into the effervescent formulation itself. In the presence of the acid component and when contacted with water the gas generating agents release carbon dioxide. Suitable acids according to the present invention may be selected from the following acids as well as partial salts of the following acids with alkaline or alkaline earth metals in the case of polybasic acids: Citric acid, tartaric acid, malic acid, adipic acid, succinic acid, fumaric acid, ascorbic acid, maleic acid, mixtures thereof. Suitable acids may be added to the effervescent formulation in about equimolar amounts as the gas generating agents.

As indicated above, in contrast to prior art delivery systems exhibiting relatively poor floating-properties, and thus requiring size expansion capability in order to securely delay passage through the pylorus, delivery systems of the present invention reliably stay afloat for several hours. Accordingly, no highly swellable polymers need to be included into the coating of the delivery systems of the present invention. Further, the absence of highly swellable polymers in the coating results in lower hygroscopicity of the coating, thus increasing shelf life and simplifying packaging of the delivery system (cf. Asian J Pharm Clin Res (2010) Vol. 3 (1), 2-10). Therefore, in a preferred embodiment of the present invention no highly swellable polymers are present in the coating of the gastric retention active delivery system. In the present context highly swellable polymers are selected from the following: agar, alginic acids and salts thereof, carrageenan, furcellaran derived from marine plants, guar gum, gum arabic, gum tragacanth, karaya gum, locust bean gum, pectin derived from terrestrial plants, dextran, gellan gum, rhamsan gum, welan gum, xanthan gum, propylene glycol alginate, hydroxypropyl guar, sodium starch glycolate, highly swellable crosslinked polymers of acrylic acid with vinyl glycol commonly known as polycarbophils, highly swellable crosslinked polyvinylpyrrolidone or crospovidone, highly swellable copolymers of vinyl pyrrolidone and vinyl acetate.

In preferred embodiments the present invention, further, comprises gastric retention active delivery system in the form of a coated capsule, consisting of a sealed capsule encasing an effervescent formulation of one or more water soluble active components A, and a coating comprising an initial dose ID of at least one of the water soluble active components A present within the sealed capsule;
wherein the coating consists of:
a total amount px of one or more pore forming components P, with px selected in the interval p1<px<p2, wherein $p1=1$ mg/cm$^2$ and $p2=11$ mg/cm$^2$;

a total amount fx of one or more flexible polymer components F, with fx selected in the interval f1<fx<f2, wherein $f1=4$ mg/cm$^2$ and $f2=10$ mg/cm$^2$, and wherein, further, $0.453*px+3.49$ mg/cm$^2$<$fx$<$0.625*px+4.75$ mg/cm$^2$;

a total amount ex of one or more amphiphilic emulsifier components E, with ex selected in the interval e1<ex<e2, wherein $e1=0$ and $e2=0.1*fx$;

a total amount tx of one or more anti-tacking components T, with tx selected in the interval t1<tx<t2, wherein $t1=0.5*fx$ and $t2=2*fx$;

a total amount nx of one or more non-water soluble excipients N, with nx selected in the interval n1<nx<n2, wherein $n1=0$ and $n2=0.1*fx$;

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;
wherein pore forming components P are defined as water soluble substances, including active components A, but excluding amphiphilic emulsifier components E;
wherein the initial dose ID, of at least one water soluble active component A present in the coating constitutes 5 wt % to 50 wt % of the total amount of this component present in the gastric retention active delivery system;
wherein, further, the effervescent formulation inside of the sealed capsule exhibits a gas generating capacity in the range of 60 Vol % to 140 Vol % of the total volume of the sealed capsule at 25° C. and 1013 mbar
with the proviso that no highly swellable polymers are present in the coating.

In other preferred embodiments the present invention, further, comprises gastric retention active delivery system in the form of a coated capsule, consisting of a sealed capsule encasing an effervescent formulation of one or more water soluble active components A, and a coating comprising an initial dose ID of at least one of the water soluble active components A present within the sealed capsule;
wherein the coating consists of:
a total amount px of one or more pore forming components P, with px selected in the interval p1<px<p2, wherein $p1=1$ mg/cm$^2$ and $p2=11$ mg/cm$^2$;

a total amount fx of one or more flexible polymer components F, with fx selected in the interval f1<fx<f2, wherein $f1=4$ mg/cm$^2$ and $f2=10$ mg/cm$^2$, and wherein, further, $$0.453*px+3.49 \text{ mg/cm}^2 < fx < 0.625*px+4.75 \text{ mg/cm}^2;$$

a total amount ex of one or more amphiphilic emulsifier components E, with ex selected in the interval $e1<ex<e2$, wherein $e1=0$ and $e2=0.1*fx$;

a total amount tx of one or more anti-tacking components T, with tx selected in the interval $t1<tx<t2$, wherein $$t1=0.5*fx \text{ and } t2=2*fx;$$

a total amount nx of one or more non-water soluble excipients N, with nx selected in the interval $n1<nx<n2$, wherein $n1=0$ and $n2=0.1*fx$;

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;

wherein pore forming components P are defined as water soluble substances, including active components A, but excluding amphiphilic emulsifier components E;

wherein the initial dose ID, of at least one water soluble active component A present in the coating constitutes 5 wt % to 50 wt % of the total amount of this component present in the gastric retention active delivery system;

wherein, further, the effervescent formulation inside of the sealed capsule exhibits a gas generating capacity in the range of 60 Vol % to 140 Vol % of the total volume of the sealed capsule at 25° C. and 1013 mbar;

wherein, further, the water soluble active components A are selected from the following: Non-amphiphilic polyphenols that can be dissolved in water at 25° C. and pH 1.2 at a concentration of at least 33 g per liter of water; and the amphiphilic emulsifier components E are non-ionic emulsifiers with an HLB-value greater than 14 selected from the following: Polysorbates, polyoxyethylated glycol monoethers, polyoxyethylated alkyl phenols; and the anti-tacking components T are selected from the following: Talc, glyceryl monostearate, kaoline, fumed silica, precipitated silica, magnesium stearate, calcium stearate, zinc stearate;

with the proviso that no highly swellable polymers are present in the coating.

In other preferred embodiments the present invention, further, comprises gastric retention active delivery system in the form of a coated capsule, consisting of a sealed capsule encasing an effervescent formulation of one or more water soluble active components A, and a coating comprising an initial dose ID of at least one of the water soluble active components A present within the sealed capsule;

wherein the coating consists of:

a total amount px of one or more pore forming components P, with px selected in the interval $p1<px<p2$, wherein $$p1=1 \text{ mg/cm}^2 \text{ and } p2=11 \text{ mg/cm}^2;$$

a total amount fx of one or more flexible polymer components F, with fx selected in the interval $f1<fx<f2$, wherein $f1=4$ mg/cm$^2$ and $f2=10$ mg/cm$^2$, and wherein, further, $$0.453*px+3.49 \text{ mg/cm}^2 < fx < 0.625*px+4.75 \text{ mg/cm}^2;$$

a total amount ex of one or more amphiphilic emulsifier components E, with ex selected in the interval $e1<ex<e2$, wherein $$e1=0 \text{ and } e2=0.1*fx;$$

a total amount tx of one or more anti-tacking components T, with tx selected in the interval $t1<tx<t2$, wherein $$t1=0.5*fx \text{ and } t2=2*fx;$$

a total amount nx of one or more non-water soluble excipients N, with nx selected in the interval $n1<nx<n2$, wherein $$n1=0 \text{ and } n2=0.1*fx;$$

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;

wherein pore forming components P are defined as water soluble substances, including active components A, but excluding amphiphilic emulsifier components E;

wherein the initial dose ID, of at least one water soluble active component A present in the coating constitutes 5 wt % to 50 wt % of the total amount of this component present in the gastric retention active delivery system;

wherein, further, the effervescent formulation inside of the sealed capsule exhibits a gas generating capacity in the range of 60 Vol % to 140 Vol % of the total volume of the sealed capsule at 25° C. and 1013 mbar;

wherein, further, the pore forming components P are selected from the following: polyphenols, maltodextrin, citric acid; and the water soluble active components A are selected from the following: Non-amphiphilic polyphenols that can be dissolved in water at 25° C. and pH 1.2 at a concentration of at least 33 g per liter of water; and the amphiphilic emulsifier components E are non-ionic emulsifiers with an HLB-value greater than 14 selected from the following: Polysorbates, polyoxyethylated glycol monoethers, polyoxyethylated alkyl phenols; and the anti-tacking components T are selected from the following: Talc, glyceryl monostearate, kaoline, fumed silica, precipitated silica, magnesium stearate, calcium stearate, zinc stearate;

with the proviso that no highly swellable polymers are present in the coating.

In other preferred embodiments the present invention, further, comprises gastric retention active delivery system in the form of a coated capsule, consisting of a sealed capsule encasing an effervescent formulation of one or more water soluble active components A, and a coating comprising an initial dose ID of at least one of the water soluble active components A present within the sealed capsule;

wherein the coating consists of:

a total amount px of one or more pore forming components P, with px selected in the interval $p1<px<p2$, wherein $$p1=1 \text{ mg/cm}^2 \text{ and } p2=11 \text{ mg/cm}^2;$$

a total amount fx of one or more flexible polymer components F, with fx selected in the interval $f1<fx<f2$, wherein $f1=4$ mg/cm$^2$ and $f2=10$ mg/cm$^2$, and wherein, further, $0.453*px+3.49$ mg/cm$^2 < fx < 0.625*px+4.75$ mg/cm$^2$;

a total amount ex of one or more amphiphilic emulsifier components E, with ex selected in the interval $e1 < ex < e2$, wherein $e1=0$ and $e2=0.1*fx$;

a total amount tx of one or more anti-tacking components T, with tx selected in the interval $t1 < tx < t2$, wherein $t1=0.5*fx$ and $t2=2*fx$;

a total amount nx of one or more non-water soluble excipients N, with nx selected in the interval $n1 < nx < n2$, wherein $n1=0$ and $n2=0.1*fx$;

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;

wherein pore forming components P are defined as water soluble substances, including active components A, but excluding amphiphilic emulsifier components E;

wherein the initial dose ID, of at least one water soluble active component A present in the coating constitutes 5 wt % to 50 wt % of the total amount of this component present in the gastric retention active delivery system;

wherein, further, the effervescent formulation inside of the sealed capsule exhibits a gas generating capacity in the range of 60 Vol % to 140 Vol % of the total volume of the sealed capsule at 25° C. and 1013 mbar;

wherein, further, the pore forming components P are selected from the following: Polyphenols, maltodextrin, citric acid; and the water soluble active components A are selected from the following: Non-amphiphilic polyphenols that can be dissolved in water at 25° C. and pH 1.2 at a concentration of at least 33 g per liter of water; and the amphiphilic emulsifier components E are non-ionic emulsifiers with an HLB-value greater than 14 selected from the following: Polysorbates, polyoxyethylated glycol monoethers, polyoxyethylated alkyl phenols; and the anti-tacking components T are selected from the following: Talc, glyceryl monostearate, kaoline, fumed silica, precipitated silica, magnesium stearate, calcium stearate, zinc stearate; and the non-water soluble excipients N are selected from the following: Pigments;

with the proviso that no highly swellable polymers are present in the coating.

In other preferred embodiments the present invention, further, comprises gastric retention active delivery system in the form of a coated capsule, consisting of a sealed capsule encasing an effervescent formulation of one or more water soluble active components A, and a coating comprising an initial dose ID of at least one of the water soluble active components A present within the sealed capsule;

wherein the coating consists of:

a total amount px of one or more pore forming components P, with px selected in the interval $p1 < px < p2$, wherein $p1=1$ mg/cm$^2$ and $p2=11$ mg/cm$^2$;

a total amount fx of one or more flexible polymer components F, with fx selected in the interval $f1 < fx < f2$, wherein $f1=4$ mg/cm$^2$ and $f2=10$ mg/cm$^2$, and wherein, further, $0.453*px+3.49$ mg/cm$^2 < fx < 0.625*px+4.75$ mg/cm$^2$;

a total amount ex of one or more amphiphilic emulsifier components E, with ex selected in the interval $e1 < ex < e2$, wherein $e1=0$ and $e2=0.1*fx$;

a total amount tx of one or more anti-tacking components T, with tx selected in the interval $t1 < tx < t2$, wherein $t1=0.5*fx$ and $t2=2*fx$;

a total amount nx of one or more non-water soluble excipients N, with nx selected in the interval $n1 < nx < n2$, wherein $n1=0$ and $n2=0.1*fx$;

wherein flexible polymer components F are defined as neutral or virtually neutral (meth)acrylate copolymers composed of 20 wt % to 40 wt % of ethyl acrylate, 60 wt % to 80 wt % of methyl methacrylate and 0 to less than 5 wt % methacrylic acid or acrylic acid;

wherein pore forming components P are defined as water soluble substances, including active components A, but excluding amphiphilic emulsifier components E;

wherein the initial dose ID, of at least one water soluble active component A present in the coating constitutes 5 wt % to 50 wt % of the total amount of this component present in the gastric retention active delivery system;

wherein, further, the effervescent formulation inside of the sealed capsule exhibits a gas generating capacity in the range of 60 Vol % to 140 Vol % of the total volume of the sealed capsule at 25° C. and 1013 mbar;

wherein, further, the pore forming components P are either non-amphiphilic substances that can be dissolved in water at 25° C. and pH 1.2 at a concentration of at least 33 g per liter of water, and which are selected from the following: Vitamins; micronutrients; inorganic salts; amino acids or keto acids; trace elements; dyes; antacids; substances obtainable from extracts of fruits and/or flowers; or the pore forming components P are non-amphiphilic substances that can be dissolved in water at 25° C. and pH 1.2 at a concentration of at least 33 g per liter of water, and which are selected from the following: Organic or inorganic salts of magnesium, sodium, calcium, potassium, lithium, ammonium; water soluble cellulose ethers; water soluble organic acids or alpha-hydroxy acids including citric acid, oxalic acid, malic acid, mandelic acid, glycolic acid, tartaric acid, fumaric acid; water-soluble sugars including polydextrose, pullulan, dextran, sucrose, glucose, fructose, mannitol, lactose, mannose, galactose, rhamnose, sorbitol, maltodextrin, trehalose, xylitol; and the water soluble active components A are non-amphiphilic substances that can be dissolved in water at 25° C. and pH 1.2 at a concentration of at least 33 g per liter of water, and which are selected from the following: Vitamins; micronutrients; inorganic salts; amino acids or keto acids; trace elements; dyes; antacids; substances obtainable from extracts of fruits and/or flowers; and the amphiphilic emulsifier components E are non-ionic emulsifiers with an HLB-value greater than 14 selected from the following: Polysorbates, polyoxyethylated glycol monoethers, polyoxyethylated alkyl phenols; and the anti-tacking components T are selected from the following: Talc, glyceryl monostearate, kaoline, fumed silica, precipitated silica, magnesium stearate, calcium stearate, zinc stearate; and the non-water soluble excipients N are selected from the following: Pigments;

with the proviso that no highly swellable polymers are present in the coating.

The present invention, further, comprises use of the gastric retention active delivery systems as disclosed for the delivery of one or more water soluble active components A to a mammal.

EXAMPLES

Materials

The following chemical compounds and equipment were used for the preparation of gastric retention active delivery systems.

TABLE 1

Chemical compounds used for preparation of powder filled capsules

| Material | Supplier |
| --- | --- |
| Elderberry extract | Plantextrakt (Vestenbergsgreuth, Germany) |
| Resveratrol | Angene International Limited (London, UK) |
| Citric acid, anhydrous | Merck KGaA (Darmstadt, Germany) |
| Sodium hydrogen carbonate | Merck KGaA (Darmstadt, Germany) |
| Microcrystalline cellulose (Avicel ® 200) | FMC Bio Polymer (Philadelphia, USA) |
| Maltodextrin (Glucidex ® 12 D) | Roquette (Lestrem, France) |
| HPMC capsules, size 3 (VCaps ® Plus) | Capsugel (Bornem, Belgium) |
| Gelatine capsules, size 3 (Coni-Snap ®) | Capsugel (Bornem, Belgium) |

TABLE 2

Chemical compounds for capsule coating

| Material | Supplier |
| --- | --- |
| HPMC (viscosity: 2-25 cPs) | Sheffield Bioscience (Norwich, USA) |
| HPMC (viscosity 2% w/w aqueous solution: 3000-5600 cPs) | Dow Chemical Company Limited (England, UK) |
| Elderberry extract | Plantextrakt (Vestenbergsgreuth, Germany) |
| Resveratrol | Angene International Limited (London, UK) |
| Maltodextrin (Glucidex ® 12 D) | Roquette (Lestrem, France) |
| Eudraguard ® control | Evonik Nutrition & Care GmbH (Darmstadt, Germany) |
| Eudraguard ® biotic | Evonik Nutrition & Care GmbH (Darmstadt, Germany) |
| Poly (Vinyl Acetate) Dispersion 30 Per Cent Ph. Eur. (Kollicoat ® SR 30 D) | BASF SE (Ludwigshafen, Germany) |
| Ethylcellulose Aqueous Dispersion (Aquacoat ® ECD-30) | FMC BioPolymer (Philadelphia, USA) |
| Talc, micronized | Merck KGaA (Darmstadt, Germany) |
| Polyoxyethylene sorbitan monooleate (Polysorbate 80) | Merck KGaA (Darmstadt, Germany) |
| Citric acid, anhydrous | Merck KGaA (Darmstadt, Germany) |
| Purified water | — |

TABLE 3

Chemical compounds for dissolution test

| Material | Supplier |
| --- | --- |
| Sodium chloride | Merck KGaA (Darmstadt, Germany) |
| Hydrochloric acid | Merck KGaA (Darmstadt, Germany) |
| Purified water | — |

TABLE 4

Devices used for production process

| Device | Provider |
| --- | --- |
| Turbula ® T 2 F, shaker mixer | Willy A. Bachofen AG (Muttenz, Switzerland) |
| Capsule filling machine including orienter | Zscheile & Klinger (Hamburg, Germany) |
| Glatt GPCG 1.1 | Glatt GmbH (Binzen, Germany) |
| Silverson High-Shear-Mixer L4RT with square hole high shear screen | Silverson Machines, Inc. (East Longmeadow, US) |
| Magnetic stirrer, Heidolph MR Hei-Mix D | Heidolph Instruments GmbH & Co. KG (Schwabach, Germany) |
| pH Meter, WTW pH 3210 | WTW—Wissenschaftlich-Technische Werstätten GmbH (Weilheim, Germany) |

TABLE 5

Devices used for analytical characterization (biological/physicochemical)

| Device | Provider |
| --- | --- |
| Dissolution tester DT 700 (USP2) | Erweka GmbH (Heusenstamm, Germany) |
| UV/VIS Spectrometer, Perkin Elmer Lambda 25 | PerkinElmer Office (Hamburg, Germany) |
| Multicheck | Erweka GmbH (Heusenstamm, Germany) |

Example 1: Determination of Suitable Amount of Gas Generating Agent (GGA)

In preliminary trials the gas generating capacity of the gas generating agent (GGA) for achieving a suitable floating behavior of the capsule was evaluated. For that, powder mixtures with different ratios of ingredients and GGA were tested.

A gas generating agent mixture containing 1 mol citric acid, anhydrous, and 1 mol sodium hydrogen carbonate was mixed for 10 min with a three-dimensional mixer. Afterwards different amounts of GGA were added to the ingredient as shown in table 6, followed by further mixing with a three-dimensional mixer for 10 min.

TABLE 6

Ingredient/GGA mixtures

| | Ingredient: GGA (% w/w) | | | |
| --- | --- | --- | --- | --- |
| Substance | 10% | 5% | 2.5% | 1% |
| Ingredient (maltodextrin) [g] | 6.85 | 7.22 | 7.41 | 7.52 |
| GGA [g] | 0.76 | 0.38 | 0.19 | 0.08 |

Each ingredient/GGA mixture was filled manually in a HPMC capsule (size 3) till maximum of capsule body (~150 mg), followed by closing with specific capsule cap and dipping in an organic poly(butyl methacrylate-co-(2-dimethylaminoethyl) methacrylate-co-methyl methacrylate) 1:2:1 suspension (Eudragit® E) containing talc as antitacking agent for complete sealing of the capsule. To compare the mixtures with different amounts of GGA, the volume ratio of maximum generated gas at standard conditions divided by the capsule volume—Vg/Vc—is of interest.

Afterwards the floating test of each coated capsule was performed in 0.1 N HCl at 37° C. One capsule was tested in 150 mL medium, followed by the observation of its floating behavior (table 7).

TABLE 7

Floating behavior for various ingredient/GGA ratios

| Ingredient: GGA (% w/w) | Vg/Vc (v/v) | Observation floating behavior |
|---|---|---|
| 10% | 4.0 | Capsule showed strong burst behavior due to high GGA content; sinking after 10 min was observed |
| 5% | 2.0 | Capsule showed leakage of gas after 12 min; sinking after 15 min was observed |
| 2.5% | 1.0 | Capsule showed suitable floating behavior for 15 min due to slow and controlled gas generation |
| 1% | 0.40 | Capsule stopped floating after 11 minutes due to low GGA content |

According to table 7, the capsule formulations containing a Vg/Vc≥2 showed a strong burst effect based on an intensive gas generating reaction, while sinking of capsules with a Vg/Vc of 0.4 was observed due to the limited gas generation. The best result for the floating behavior of the capsule was obtained with a Vg/Vc of 1.

Our observations revealed that a Vg/Vc of 0.4 is not sufficient for receiving the desired capsule floating behavior and a Vg/Vc of 2.0 leads to a burst of the capsule. Based on these results, the Vg/Vc must be in a range of 0.6-1.4, which corresponds to Vg/Vc=1.0±40%.

Example 2: Mixture of Powders and Capsule Filling

Gas Generating Agent Pre-Mixture:

19.21 g of citric acid and 8.40 g of sodium hydrogen carbonate were filled into a 50 mL PE bottle and mixed with a shaker mixer for 10 min at a speed of 49 $min^{-1}$.

Final Powder Mixture:

350 g of elderberry extract and 8.97 g of prepared gas generating agent pre-mixture were filled into a 1 L PE bottle and mixed with a shaker mixer for 10 min at a speed of 49 $min^{-1}$.

Capsule Filling:

The capsule filling machine was set up and filled with empty HPMC capsules. The caps were removed and the final mixed powder was filled into the capsules up to the maximum volume.

Afterwards the capsules were closed.

Weight Uniformity:

Thirty capsules were analyzed using Erweka Multicheck. As a result a final capsule weight of around 200 mg was achieved. The deviation of each capsule from the average mass of 20 capsules was less than 10%. Therefore, the uniformity of weight complies the demands of the European Pharmacopoeia (2.9.5.).

Example 3: Capsule Sealing (Subcoat)

In order to seal the capsules a subcoat was applied. A standard fluid bed coating technique was applied as described in Eudragit® Application Guidelines, $12^{th}$ Edition.

Manufacturing of Coating Dispersion

TABLE 8

| Subcoat formulation | | |
|---|---|---|
| Compound | Quantity [g] | Dry substance [g] |
| HPMC (viscosity: 2-25 cPs) | 57.3 | 57.3 |
| Purified water | 515.7 | XX |

57.3 g of HPMC (viscosity: 2-25 cPs) (Sheffcoat Clear VLV, Sheffield Bioscience) were dissolved in 515.7 g purified water with a dissolver disk. 420 g of filled capsules size 3 (199.6 mg/capsule) were coated in Glatt GPCG1.1 using bottom spray insert. Coating level was set to 9.4 mg/$cm^2$ total solids. This coating level was determined in a previous study. Coating temperature was set to product recommendations from supplier.

Coating Process for Subcoat:

The HPMC solution was sprayed onto 420 g of capsules in a Glatt GPCG 1.1 at the following parameters:

TABLE 9

| Process parameters for subcoating | | |
|---|---|---|
| Parameter | Unit | Range |
| Inlet air temperature | [° C.] | 29-31 |
| Product temperature | [° C.] | 22-24 |
| Inlet air flow | [$m^3$/h] | 138-142 |
| Spray rate | [g/min] | 7.3-12.8 |
| Atomization pressure | [bar] | 2.0 |
| Coating time | [min] | 54 |

The filled and sealed capsules (Example 2+3) were used as starting material for following coating examples 4-7.

Examples 4, 5 & 6 are comprising a design of experiments study to determine the ratio of pore forming component (p) and flexible film forming component (f).

Example 4: Eudraguard® Control Functional Top Coating—According to the Invention

TABLE 10

| Coating formulation Eudraguard ® control | | |
|---|---|---|
| Compound | Quantity [g] | Dry substance [g] |
| Eudraguard ® control | 156.7 | 47.0 |
| Talc, micronized | 35.2 | 35.2 |
| Polysorbate 80 33% (w/w aq.) | 14.2 | 4.7 |
| Elderberry extract | 42.3 | 42.3 |
| Purified water | 613.2 | — |

Manufacturing of Coating Dispersion

Eudraguard® control dispersion was diluted to 20% solid content with demineralized water. Afterwards polysorbate 80 solution 33% (w/w) was poured into the Eudraguard® control dispersion while stirring with an overhead stirrer. The pH of this dispersion was adjusted to pH 3.6 using citric acid solution 20% (w/w). Talc and elderberry extract were homogenized in the remaining demineralized water for at least 10 min using an Ultra Turrax. The dispersion containing talc and extract was slowly poured into the polymer dispersion while stirring with an overhead stirrer. The final dispersion was stirred for at least 15 min and passed through a 0.5 mm sieve prior to the coating procedure. The total solid content in the final dispersion was 15% (w/w).

Example 5: Eudraguard® Control Functional Top Coating—Comparative Example

TABLE 11

| Coating formulation Eudraguard ® control | | |
|---|---|---|
| Compound | Quantity [g] | Dry substance [g] |
| Eudraguard ® control | 200.3 | 60.1 |
| Talc, micronized | 45.1 | 45.1 |
| Polysorbate 80 33% (w/w aq.) | 18.2 | 6.0 |
| Elderberry extract | 18.0 | 18.0 |
| Purified water | 579.6 | |

Manufacturing of Coating Dispersion

Eudraguard® control dispersion was diluted to 20% solid content with demineralized water. Afterwards polysorbate 80 solution 33% (w/w) was poured into the Eudraguard® control dispersion while stirring with an overhead stirrer. The pH of this dispersion was adjusted to pH 3.6 using citric acid solution 20% (w/w). Talc and elderberry extract were homogenized in the remaining demineralized water for at least 10 min using an Ultra Turrax. The dispersion containing talc and extract was slowly poured into the polymer dispersion while stirring with an overhead stirrer. The final dispersion was stirred for at least 15 min and passed through a 0.5 mm sieve prior to the coating procedure. The total solid content in the final dispersion was 15% (w/w).

Example 6: Eudraguard® Control Functional Top Coating—Comparative Example

TABLE 12

| Coating formulation Eudraguard ® control | | |
|---|---|---|
| Compound | Quantity [g] | Dry substance [g] |
| Eudraguard ® control | 128.6 | 38.6 |
| Talc, micronized | 28.9 | 28.9 |
| Polysorbate 80 (33% w/w aq.) | 11.7 | 3.9 |
| Elderberry extract | 57.9 | 57.9 |
| Purified water | 634.5 | |

Manufacturing of Coating Dispersion

Eudraguard® control dispersion was diluted to 20% solid content with demineralized water. Afterwards polysorbate 80 solution 33% (w/w) was poured into the Eudraguard® control dispersion while stirring with an overhead stirrer. The pH of this dispersion was adjusted to pH 3.6 using citric acid solution 20% (w/w). Talc and elderberry extract were homogenized in the remaining demineralized water for at least 10 min using an Ultra Turrax. The dispersion containing talc and extract was slowly poured into the polymer dispersion while stirring with an overhead stirrer. The final dispersion was stirred for at least 15 min and passed through a 0.5 mm sieve prior to the coating procedure. The total solid content in the final dispersion was 15% (w/w).

Coating Processes for Examples 4-6

The coating dispersion was sprayed onto 420 g of previously sealed capsules in a Glatt GPCG 1.1 fluid bed coater at the parameters shown in table 13:

TABLE 13

| Process parameters | | | | |
|---|---|---|---|---|
| Parameter | Unit | Example 4 | Example 5 | Example 6 |
| Inlet air temperature | [° C.] | 29-31 | 29-31 | 26-30 |
| Product temperature | [° C.] | 23-25 | 23-25 | 21-25 |
| Inlet air flow | [m³/h] | 138-142 | 142-148 | 140-163 |
| Spray rate | [g/min] | 8.5-13.5 | 8.3-13.9 | 8.4-10.2 |
| Atomisation pressure | [bar] | 2.0 | 2.0 | 2.0 |
| Coating time | [min] | 79 | 79 | 84 |

The final coating level was 21.2 mg/cm² based on the amount of total solids, samples were withdrawn from the process at 12.9 and 17.05 mg/cm².

Release

Dissolution test was performed using the USP II apparatus. As dissolution media 500 mL of simulated gastric fluid (pH 1.2) were used. The temperature was maintained at 37° C. 4-0.5° C. and the paddles were rotated at 75 rpm. Samples were collected every 15 min till 2 h, followed by every 30 min till 3 h. The final sample was collected after 4 h. 2 mL of the dissolution media were removed manually. The obtained samples were measured spectrophotometrically at 515 nm. Additionally the observation, if the capsules floated correctly.

TABLE 14

| Release profiles examples 4 | | | | | | |
|---|---|---|---|---|---|---|
| Time[min] | Example 4 12.9 mg/cm² | Example 4/ 17.05 mg/cm² | Example 4 21.2 mg/cm² | Example 4 12.9 mg/cm² | Example 4 17.05 mg/cm² | Example 4 21.2 mg/cm² |
| 0 | 0.2 | 0.2 | 0.4 | 0.1 | 0.2 | 0.2 |
| 30 | 4.3 | 5.2 | 6.3 | 4.1 | 5.3 | 6.6 |
| 45 | 5.9 | 5.9 | 7.8 | 11.3 | 6.0 | 8.2 |

TABLE 14-continued

Release profiles examples 4

| Time[min] | Example 4 12.9 mg/cm² | Example 4/ 17.05 mg/cm² | Example 4 21.2 mg/cm² | Example 4 12.9 mg/cm² | Example 4 17.05 mg/cm² | Example 4 21.2 mg/cm² |
| --- | --- | --- | --- | --- | --- | --- |
| 60 | 30.9 | 8.6 | 7.9 | 45.7 | 10.0 | 8.8 |
| 75 | 67.5 | 40.5 | 10.2 | 68.1 | 24.1 | 21.5 |
| 90 | 89.5 | 54.0 | 14.8 | 82.7 | 37.3 | 33.6 |
| 105 | 95.6 | 68.2 | 23.5 | 94.0 | 62.4 | 43.2 |
| 120 | 97.0 | 83.9 | 38.3 | 98.0 | 81.3 | 58.9 |
| 150 | 99.8 | 95.2 | 65.0 | 99.8 | 88.3 | 89.8 |
| 180 | 100.7 | 96.8 | 78.6 | 100.9 | 89.5 | 94.3 |
| 240 | 101.4 | 99.5 | 89.2 | 101.7 | 99.8 | 97.7 |
| 243 | 100.0 | 100.0 | 100.0 | 100.0 | 100.0 | 100.0 |
| Floating time >2 h | No | No | Yes | No | No | Yes |

TABLE 15

Release profiles examples 5-6

| time[min] | Example 6 12.9 mg/cm² | Example 6 17.05 mg/cm² | Example 6 21.2 mg/cm² | Example 5 12.9 mg/cm² | Example 5 17.05 mg/cm² | Example 5 21.2 mg/cm² |
| --- | --- | --- | --- | --- | --- | --- |
| 0 | 0.1 | 0.0 | 0.1 | 0.1 | 0.1 | 0.2 |
| 30 | 7.0 | 8.0 | 8.9 | 1.3 | 1.2 | 1.3 |
| 45 | 14.8 | 12.5 | 10.3 | 1.5 | 1.3 | 1.5 |
| 60 | 76.8 | 43.5 | 17.3 | 1.8 | 1.5 | 1.7 |
| 75 | 91.5 | 65.9 | 65.2 | 1.5 | 1.5 | 1.7 |
| 90 | 94.8 | 81.6 | 89.0 | 1.3 | 1.6 | 1.7 |
| 105 | 96.2 | 93.6 | 93.8 | 1.5 | 1.7 | 1.9 |
| 120 | 97.3 | 96.7 | 96.0 | 1.8 | 1.8 | 2.1 |
| 150 | 98.5 | 98.0 | 97.2 | 5.1 | 2.0 | 2.1 |
| 180 | 99.3 | 98.4 | 98.1 | 9.3 | 6.2 | 2.3 |
| 240 | 99.5 | 99.9 | 98.1 | 45.0 | 43.7 | 3.2 |
| 243 | 100.0 | 100.0 | 99.0 | 100.0 | 100.0 | 100.0 |
| Floating time >2 h | No | No | No | Yes | Yes | Yes |

To secure a delivery to the stomach the capsules need to show sufficient buoyancy over a time period of >2 h hours, while simultaneously releasing the drug without sinking. This behavior was observed in case of example 4 at a coating level of 21.2 mg/cm² based on the amount of total solids. It correlated to a release onset of 75 respectively 80 min. Release onset is the time point at which the capsules started to release the inner filling.

Since the sampling took place every 15 min and a release onset of 60 min was correlated with a capsule sinking—example 4 17.05 mg/cm² base on the amount of total solids, the target window for analyzing the design of experiments study was set to 70-105 min.

Subsequently, the window for a release profile is defined as follows: Release of 5% to 55% of the total amount present in the gastric retention system at t=105 min after administration; and release of 47%-96% of the total amount present in the gastric retention system at t=180 min after administration; and release of 70%-100% of the total amount present in the gastric retention system at t=240 min after administration.

TABLE 16

Design of experiments data table

| Exp No | Patent Example No./Coating Level | Coating level pore forming component [mg/cm²] | Coating level flexible polymer component [mg/cm²] | Release onset [min] |
| --- | --- | --- | --- | --- |
| 1 | 5/12.9 | 1.80 | 6 | 120 |
| 2 | 6/12.9 | 5.78 | 3.85 | 35 |
| 3 | 5/21.2 | 2.96 | 9.86 | 220 |
| 4 | 6/21.2 | 9.45 | 6.3 | 50 |
| 5 | 5/17.05 | 2.38 | 7.93 | 150 |
| 6 | 6/17.05 | 7.65 | 5.1 | 45 |
| 7 | 4/12.9 | 4.22 | 4.69 | 35 |
| 8 | 4/21.2 | 6.93 | 7.7 | 75 |
| 9 | 4/12.9 | 4.22 | 4.69 | 45 |
| 10 | 4/17.05 | 5.58 | 6.2 | 60 |
| 11 | 4/21.2 | 6.93 | 7.7 | 80 |
| 12 | 4/17.05 | 5.58 | 6.2 | 60 |

The design was analysed using a multiple linear regression method (ICH HARMONISED TRIPARTITE GUIDELINE—PHARMACEUTICAL DEVELOPMENT—Q8 (R2)—Current Step 4 version—dated August 2009) in order to identify boundary functions describing the limits of suitable correlation between the amount of pore forming components and the amount of flexible polymer components. The following relations were found to delimit correlations between the amount of pore forming components and the amount of flexible polymer components yielding desirable floating and release properties as outlined above:
  px=total amount of pore forming components,
  fx=total amount of flexible polymer components,
  p1<px<p2 with p1=1 mg/cm² and p2=11 mg/cm², and
  f1<fx<f2 with f1=4 mg/cm² and f2=10 mg/cm², and
  0.453*px+3.49 mg/cm²<fx<0.625*px+4.75 mg/cm².

Example 7—According to the Invention

Gelatin capsules were filled and sealed according to Examples 2-3 and used as starting

TABLE 17

Coating formulation

| Compound | Quantity [g] | Dry substance [g] |
|---|---|---|
| Eudraguard ® control | 196.3 | 58.9 |
| Talc, micronized | 44.2 | 44.2 |
| Polysorbate 80 (33% w/w aq.) | 17.8 | 5.9 |
| Elderberry Extract | 53.0 | 53.0 |
| Purified water | 768.5 | |

Manufacturing of Coating Dispersion

Eudraguard® control dispersion was diluted to 20% solid content with demineralized water. Afterwards polysorbate 80 solution 33% (w/w) was poured into the Eudraguard® control dispersion while stirring with an overhead stirrer. The pH of this dispersion was adjusted to pH 3.6 using citric acid solution 20% (w/w). Talc and elderberry extract were homogenized in the remaining demineralized water for at least 10 min using an Ultra Turrax. The dispersion containing talc and elderberry extract was slowly poured into the polymer dispersion while stirring with an overhead stirrer. The final dispersion was stirred for at least 15 min and passed through a 0.5 mm sieve prior to the coating procedure. The total solid content in the final dispersion was 15% (w/w).

Coating Process

The coating dispersion was sprayed onto previously sealed capsules in a Glatt GPCG 1.1 at the following parameters:

TABLE 18

Process parameters

| Parameter | Unit | Range |
|---|---|---|
| Inlet air temperature | [° C.] | 28-32 |
| Product temperature | [° C.] | 24-25 |
| Inlet air flow | [m³/h] | 150-157 |
| Spray rate | [g/min] | 8-11 |
| Atomisation pressure | [bar] | 2.0 |
| Coating time | [min] | 113 |

The final coating level was 21.2 mg/cm² based on the amount of total solids.

Release

Dissolution test was performed using the USP II apparatus. As dissolution media 500 mL of simulated gastric fluid (pH 1.2) were used. The temperature was maintained at 37° C.±0.5° C. and the paddles were rotated at 75 rpm.

Samples were collected every 15 min till 2 h, followed by every 30 min till 3 h. The final sample was collected after 4 h. 2 mL of the dissolution media were removed manually. The obtained samples were measured spectrophotometrically at 515 nm.

TABLE 19

Release profile

| Time [min] | Example 7 Release [%] |
|---|---|
| 0 | 0 |
| 30 | 8.3 |
| 45 | 8.9 |
| 60 | 9.5 |
| 75 | 14 |
| 90 | 26 |
| 105 | 35 |
| 120 | 43 |
| 150 | 55 |
| 180 | 62 |
| 240 | 72 |

Examples 8-10 as Comparative Examples

The filled and sealed capsules (Examples 2-3) were used as starting material for following comparative coating examples 8-10.

Example 8: Aquacoat® ECD Functional Coating

TABLE 20

Coating formulation

| Compound | Quantity [g] | Dry substance [g] |
|---|---|---|
| Ethylcellulose aqueous dispersion (Aquacoat ® ECD-30) | 156.8 | 47.0 |
| Talc, micronized | 35.2 | 35.2 |
| Polysorbate 80 33% (w/w aq.) | 14.2 | 4.7 |
| Elderberry extract | 42.3 | 43.3 |
| Purified water | 623.3 | |

Manufacturing of Coating Dispersion

The Ethylcellulose Aqueous Dispersion (Aquacoat® ECD-30) was diluted to 20% (w/w) with demineralized water. Afterwards polysorbate 80 was dissolved in 50 g of demineralized water and added to the ethylcellulose dispersion. The pH of this dispersion was adjusted to pH 3.6 using citric acid solution 20% (w/w). Talc and elderberry extract were homogenized in the remaining amount of demineralized water for 30 min using an Ultra Turrax and afterwards slowly added to the polymer dispersion while stirring with an overhead stirrer. The resulting suspension was further stirred for 30 min. The final suspension was passed through a 0.5 mm sieve prior to the coating procedure.

Example 9—Comparative: Kollicoat SR 30 D Functional Top Coating

TABLE 21

Coating formulation

| Compound | Quantity [g] | Dry substance [g] |
|---|---|---|
| Poly (Vinyl Acetate) dispersion 30% (Kollicoat ® SR 30 D) | 156.8 | 47.0 |
| Talc, micronized | 35.2 | 35.2 |

TABLE 21-continued

| Coating formulation | | |
|---|---|---|
| Compound | Quantity [g] | Dry substance [g] |
| Polysorbate 80 | 4.7 | 4.7 |
| Elderberry extract | 42.3 | 42.3 |
| Purified water | 1054.5 | |

Manufacturing of Coating Dispersion

Poly (Vinyl Acetate) Dispersion 30% (Kollicoat® SR 30 D) was diluted to 10% (w/w) with demineralized water. Afterwards polysorbate 80 was dissolved in 50 g of demineralized water and added to the poly (vinyl acetate) dispersion. The pH of this dispersion was pH 3.0. Talc and elderberry extract were homogenized in the remaining amount of demineralized water for 30 min using an Ultra Turrax and afterwards slowly added to the polymer dispersion while stirring with an overhead stirrer. The resulting suspension was further stirred for 30 min. The final suspension was passed through a 0.5 mm sieve prior to the coating procedure.

Example 10—Comparative: Eudraguard® Biotic Functional Top Coating

TABLE 22

| Coating Formulation | | |
|---|---|---|
| Compound | Quantity [g] | Dry substance [g] |
| Eudraguard ® biotic | 156.8 | 47.0 |
| Talc, micronized | 35.2 | 35.2 |
| Polysorbate 80 | 4.7 | 4.7 |
| Elderberry extract | 42.3 | 43.3 |
| Purified water | 623.3 | — |

Manufacturing of Coating Dispersion

Eudraguard® biotic was diluted to 5% (w/w) with demineralized water. Afterwards polysorbate 80 was dissolved in 50 g of demineralized water and added to the aqueous dispersion. The pH of this dispersion was pH 2.4. Talc and elderberry extract were homogenized in the remaining amount of demineralized water for 30 min using an Ultra Turrax and afterwards slowly added to the polymer dispersion while stirring with an overhead stirrer. The resulting suspension was further stirred for 30 min. The final suspension was passed through a 0.5 mm sieve prior to the coating procedure.

Processes for Comparative Examples 8-10

The coating dispersion was sprayed onto 420 g of previously sealed capsules in a Glatt GPCG 1.1 fluid bed coater at the following parameters:

TABLE 23

| Process Parameters | | | | |
|---|---|---|---|---|
| Parameter | Unit | Example 8 | Example 9 | Example 10 |
| Inlet air temperature | [° C.] | 39-41 | 39-40 | 28-34 |
| Product temperature | [° C.] | 32-34 | 32-34 | 28-30 |
| Inlet air flow | [m³/h] | 138-142 | 180-220 | 180-220 |
| Spray rate | [g/min] | 8-13 | 3-10 | 3-7 |
| Atomisation pressure | [bar] | 2.0 | 2.0 | 2.0 |
| Coating time | [min] | 90 | 180 | 300 |

The final coating level was 21.2 mg/cm² based on the amount of total solids.

Release Comparison

Dissolution test was performed using the USP II apparatus. As dissolution media 750 mL of simulated gastric fluid (pH 1.2) were used. The temperature was maintained at 37° C.±0.5° C. and the paddles were rotated at 50 rpm.

Samples were collected every 15 min till 2 h, followed by every 30 min till 3 h. The final sample was collected after 4 h. 2 mL of the dissolution media were removed manually. The obtained samples were measured spectrophotometrically at 512 nm.

TABLE 24

| Release Profiles | | | | |
|---|---|---|---|---|
| time min | Example 3 Release [%] | Example 6 Release [%] | Example 7 Release [%] | Example 8 Release [%] |
| 0 | 0 | 0 | 0 | 0 |
| 30 | 6.6 | 8.9 | 8.2 | 6.2 |
| 45 | 7.4 | 52 | 29 | 6.6 |
| 60 | 8.7 | 97 | 78 | 6.9 |
| 75 | 10 | 100 | 99 | 7.6 |
| 90 | 20 | 101 | 101 | 8.9 |
| 105 | 31 | 101 | 102 | 12 |
| 120 | 41 | 102 | 102 | 15 |
| 150 | 71 | 102 | 102 | 28 |
| 180 | 78 | 102 | 102 | 39 |
| 240 | 86 | 102 | 103 | 45 |
| Floating time > 2 h | Yes | No | No | Yes |

The difference in the release profiles to table 24 show, that only Eudraguard® control is providing the properties to achieve the desired release profile.

Enteric polymers like Eudraguard Biotic can not provide release because of acidic pH of anthocyanines.

Example 11—Comparative—Resveratrol as Non Water Soluble Polyphenol

Mixture of Powder for Capsule Filling

The gas generating agent pre-mixture was prepared according to Example 2. 24 g of resveratrol, 9.05 g of gas generating agent pre-mixture and 267.0 g microcrystalline cellulose were filled into a 1 L PE bottle and mixed with a shaker mixer for 10 min at a speed of 49 min⁻¹. The capsules were filled and sealed according to Example 2-3 and used as starting material for the following comparative coating example.

TABLE 25

| Coating formulation | | |
|---|---|---|
| Compound | Quantity [g] | Dry substance [g] |
| Eurdraguard ® control | 160.0 | 48.0 |
| Talc, micronized | 36.0 | 36.0 |
| Polysorbate 80 33% (w/w aq.) | 14.5 | 4.8 |
| Resveratrol | 4.6 | 4.6 |
| Maltodextrin | 38.6 | 38.6 |
| Purified water | 626.2 | |

Manufacturing of Coating Dispersion

Eudraguard® control dispersion was diluted to 20% solid content with demineralized water. Afterwards polysorbate 80 solution 33% (w/w) was poured into the Eudraguard® control dispersion while stirring with an overhead stirrer. Talc, resveratrol and maltodextrin were homogenized in the remaining demineralized water for at least 10 min using an Ultra Turrax. The dispersion containing talc, resveratrol and maltodextrin was slowly poured into the polymer dispersion while stirring with an overhead stirrer. The final dispersion was stirred for at least 15 min and passed through a 0.5 mm sieve prior to the coating procedure. The total solid content in the final dispersion was 15% (w/w).

Coating Process

The coating dispersion was sprayed onto previously sealed capsules in a Glatt GPCG 1.1 at the following parameters:

TABLE 26

Process Parameters

| Parameter | Unit | Range |
|---|---|---|
| Inlet air temperature | [° C.] | 30-32 |
| Product temperature | [° C.] | 24-25 |
| Inlet air flow | [m³/h] | 118-122 |
| Spray rate | [g/min] | 7.5-11 |
| Atomisation pressure | [bar] | 2.0 |
| Coating time | [min] | 87 |

The final coating level was 21.2 mg/cm² based on the amount of total solids.

Release

Dissolution test was performed using the USP II apparatus. As dissolution media 500 mL of simulated gastric fluid (pH 1.2) were used. The temperature was maintained at 37° C.±0.5° C. and the paddles were rotated at 75 rpm.

Samples were collected every 15 min till 2 h, followed by every 30 min till 3 h. The final sample was collected after 4 h. 2 mL of the dissolution media were removed manually. The obtained samples were measured spectrophotometrically at 305 nm.

TABLE 27

Release Profile

| Time [min] | Example 11 Release [%] |
|---|---|
| 0 | 0.2 |
| 30 | 0.2 |
| 45 | 0.1 |
| 60 | 0.1 |
| 75 | 0.1 |
| 90 | 0.1 |
| 105 | 0.8 |
| 120 | 0.5 |
| 150 | 0.6 |
| 180 | 0.3 |
| 240 | 0.4 |
| Floating time > 2 h | Yes |

The invention claimed is:

1. A gastric retention active delivery system in the form of a coated capsule, comprising a sealed capsule encasing an effervescent formulation comprising at least one water soluble active component A, and a coating, wherein:

the coating comprises:

a total amount px of at least one pore forming component P, in which the total amount px satisfies:

$p1<px<p2$, where p1=1 mg/cm² and p2=11 mg/cm²;

a total amount fx of at least one flexible polymer component F, wherein the total amount px and the total amount fx satisfy:

$0.453*px+3.49$ mg/cm² $<fx<0.625*px+4.75$ mg/cm²;

a total amount ex of at least one amphiphilic emulsifier component E, in which the total amount ex satisfies:

$e1<ex<e2$, where e1=0 and e2=0.1*fx;

a total amount tx of at least one anti-tacking component T, in which the total amount tx satisfies:

$t1<tx<t2$, where t1=0.5*fx and t2=2*fx; and a total amount nx of at least one non-water soluble excipient N, in which the total amount nx satisfies:

$n1<nx<n2$, where n1=0 and n2=0.1*fx;

the flexible polymer component F is a neutral or virtually neutral (meth)acrylate copolymer comprising 20 wt % to 40 wt % of ethyl acrylate, 60 wt % to 80 wt % of methyl methacrylate and 0 to less than 5 wt % methacrylic acid or acrylic acid;

the pore forming component P is a water soluble substance comprising the at least one active component A, but excluding the amphiphilic emulsifier component E; and the effervescent formulation inside of the sealed capsule exhibits a gas generating capacity ranging from 60 Vol % to 140 Vol % of a total volume of the sealed capsule at 25° C. and 1013 mbar.

2. The gastric retention active delivery system according to claim 1, wherein the coating comprises an initial dose ID of the at least one water soluble active component A present within the sealed capsule, and the initial dose ID constitutes 5 wt % to 50 wt % of the total amount of the at least one water soluble active component A present in the gastric retention active delivery system.

3. The gastric retention active delivery system according to claim 2, consisting of the sealed capsule and the coating, wherein the coating is free of highly swellable polymers.

4. The gastric retention active delivery system according to claim 3, wherein:

the at least one pore forming component P is selected from the group consisting of a polyphenol, maltodextrin and citric acid;

the at least one water soluble active component A is a non-amphiphilic polyphenol that can be dissolved in water at 25° C. and pH 1.2 at a concentration of at least 33 g per liter of water;

the at least one amphiphilic emulsifier component E is a non-ionic emulsifier having an HLB-value greater than 14 and is selected from the group consisting of a polysorbate, a polyoxyethylated glycol monoether and a polyoxyethylated alkyl phenol; and the at least one anti-tacking component T is selected from the group consisting of talc, glyceryl monostearate, kaoline, fumed silica, precipitated silica, magnesium stearate, calcium stearate, and zinc stearate.

5. The gastric retention active delivery system according to claim 3, wherein:

the at least one pore forming component P is selected from the group consisting of a polyphenol, maltodextrin, and citric acid;

the at least one water soluble active component A is a non-amphiphilic polyphenol that can be dissolved in water at 25° C. and pH 1.2 at a concentration of at least 33 g per liter of water;

the at least one amphiphilic emulsifier component E is a non-ionic emulsifier having an HLB-value greater than 14 and is selected from the group consisting of a polysorbate, a polyoxyethylated glycol monoether and a polyoxyethylated alkyl phenol;

the at least one anti-tacking component T is selected from the group consisting of talc, glyceryl monostearate, kaoline, fumed silica, precipitated silica, magnesium stearate, calcium stearate, and zinc stearate; and the at least one non-water soluble excipient N is a pigment.

6. The gastric retention active delivery system according to claim 3, wherein:

the at least one pore forming component P is either a non-amphiphilic substance that can be dissolved in water at 25° C. and pH 1.2 at a concentration of at least 33 g per liter of water, and which is selected from the group consisting of a vitamin, a micronutrient, an inorganic salt, an amino acid, a keto acid, a trace element, a dye, an antacid and a substance obtained from an extract of a fruit, a flower, or both, or the at least one pore forming component P is a non-amphiphilic substance that can be dissolved in water at 25° C. and pH 1.2 at a concentration of at least 33 g per liter of water, and which is selected from the group consisting of organic or inorganic salts of magnesium, sodium, calcium, potassium, lithium, ammonium; a water soluble cellulose ether; a water soluble organic acid or an alpha-hydroxy acid; a-water-soluble sugar;

the at least one water soluble active component A is a non-amphiphilic substance that can be dissolved in water at 25° C. and pH 1.2 at a concentration of at least 33 g per liter of water, and which is selected from the group consisting of a vitamin, a micronutrient, an inorganic salt, an amino acid, a keto acid, a trace element, a dye, an antacid, and a substance obtained from extracts of a fruit, a flower, or both;

the at least one amphiphilic emulsifier component E is a non-ionic emulsifier having an HLB-value greater than 14 and is selected from the group consisting of a polysorbate, a polyoxyethylated glycol monoether and a polyoxyethylated alkyl phenol;

the at least one anti-tacking component T is selected from the group consisting of talc, glyceryl monostearate, kaoline, fumed silica, precipitated silica, magnesium stearate, calcium stearate, and zinc stearate; and the at least one non-water soluble excipient N is a pigment.

7. A process, comprising delivering at least one water soluble active component A to a mammal with the gastric retention active delivery system of claim 1.

8. The gastric retention active delivery system according to claim 1, wherein:

p1=2 mg/cm$^2$ and p2=8 mg/cm$^2$.

9. The gastric retention active delivery system according to claim 1, wherein the effervescent formulation inside of the sealed capsule exhibits a gas generating capacity ranging from 80 Vol % to 120 Vol % of the total volume of the sealed capsule at 25° C. and 1013 mbar.

10. The gastric retention active delivery system according to claim 1, wherein the at least one amphiphilic emulsifier component E present in the coating is at least one non-ionic emulsifier with an HLB-value greater than 14 selected from the group consisting of a polysorbate, a polyoxyethylated glycol monoether and a polyoxyethylated alkyl phenol.

11. The gastric retention active delivery system according to claim 1, wherein the at least one anti-tacking component T present in the coating is selected from the group consisting of talc glyceryl monostearate, kaoline, fumed silica, precipitated silica, magnesium stearate, calcium stearate, and zinc stearate.

12. The gastric retention active delivery system according to claim 1, wherein the at least one water soluble active component A comprises a non-amphiphilic substance obtained from at least one plant extract.

13. The gastric retention active delivery system according to claim 1, wherein the at least one water soluble active component A comprises a non-amphiphilic polyphenol.

14. The gastric retention active delivery system according to claim 1, wherein all of the at least one water soluble active component A is selected from the group consisting of cyanidin, delphinidin, isopeonidin, peonidin, malvidin, pelargonidin, petunidin, and derivatives thereof, the derivatives obtained by substituting one or more hydroxyl groups with a mono- or oligosaccharide comprising at least one sugar selected from the group consisting of glucose, rhamnose, galactose, rutinose, and arabinose.

15. The gastric retention active delivery system according to claim 1, wherein all of the at least one water soluble active component A are non-amphiphilic substances that can be dissolved in water at 25° C. and pH 1.2 at a concentration of at least 33 g per liter of water, and which are selected from the group consisting of a vitamin, a micronutrient, an inorganic salt, an amino acid, a keto acid, a trace element, a dye, an antacid, and a substance obtained from an extract of a fruit, flower, or both.

16. The gastric retention active delivery system according to claim 3, wherein:

the at least one water soluble active component A is a non-amphiphilic polyphenol that can be dissolved in water at 25° C. and pH 1.2 at a concentration of at least 33 g per liter of water; and the at least one amphiphilic emulsifier component E is a non-ionic emulsifier having an HLB-value greater than 14 and is selected from the group consisting of a polysorate, a polyoxyethylated glycol monoether and a polyoxyethylated alkyl phenol; and the at least one anti-tacking component T is selected from the group consisting of talc, glyceryl monostearate, kaoline, fumed silica, precipitated silica, magnesium stearate, calcium stearate, and zinc stearate.

* * * * *